US012761181B2

(12) United States Patent
Zhang et al.

(10) Patent No.: US 12,761,181 B2
(45) Date of Patent: Oct. 13, 2026

(54) FET GAS SENSOR DEVICE WITH A SPACE BETWEEN A GATE AND A SEMICONDUCTOR CHANNEL HAVING AN EMBEDDED METAL NANOPARTICLE LAYER THEREON

(71) Applicant: SWESENSI AB, Sollentuna (SE)

(72) Inventors: Zhen Zhang, Sollentuna (SE); Qitao Hu, Mountain View, CA (US)

(73) Assignee: SWESENSI AB, Sollentuna (SE)

( * ) Notice: Subject to any disclaimer, the term of this patent is extended or adjusted under 35 U.S.C. 154(b) by 0 days.

(21) Appl. No.: 18/874,322

(22) PCT Filed: Jun. 14, 2023

(86) PCT No.: PCT/EP2023/066011
§ 371 (c)(1),
(2) Date: Dec. 12, 2024

(87) PCT Pub. No.: WO2023/242297
PCT Pub. Date: Dec. 21, 2023

(65) Prior Publication Data

US 2025/0164439 A1 May 22, 2025

(30) Foreign Application Priority Data

Jun. 15, 2022 (SE) .................................... 2230197-2
Dec. 16, 2022 (SE) .................................... 2251480-6

(51) Int. Cl.
*G01N 27/414* (2006.01)
*G01N 33/00* (2006.01)

(52) U.S. Cl.
CPC ....... *G01N 27/4143* (2013.01); *G01N 33/005* (2013.01)

(58) Field of Classification Search
CPC ......................... G01N 27/4143; G01N 33/005
(Continued)

(56) References Cited

U.S. PATENT DOCUMENTS 4,158,807 A * 6/1979 Senturia ............... H10D 64/311 257/253
4,411,741 A * 10/1983 Janata ................ G01N 27/4141 257/253

(Continued)

FOREIGN PATENT DOCUMENTS

CN 114597219 A * 6/2022
DE 4333875 A1 * 4/1995 ......... G01N 27/4143

(Continued)

OTHER PUBLICATIONS

Santoruvo, G. et al, IEEE Electron Device Letters 2017, 38, 1413-1416. (Year: 2017).*

(Continued)

*Primary Examiner* — Arlen Soderquist
(74) *Attorney, Agent, or Firm* — MOSER TABOADA

(57) ABSTRACT

A field effect transistor, FET, gas sensor device (100) arranged to sense gas, and a method of sensing gas by a FET gas sensor device, are provided. The FET gas sensor device comprises at least one gate (110*a*, 110*b*), a source (120), a drain (130), and a semiconductor channel (140). The semiconductor channel and the gate(s) form a FET channel-gate coupling (150) by which an applied gate potential is arranged to control a current flowing through the semiconductor channel. The FET gas sensor device further comprises space(s) (200) arranged between the gate(s) and the semiconductor channel and configured to receive gas, whereby received gas is arranged to influence electrical property(ies) of the FET channel-gate coupling, and wherein the FET gas sensor device is arranged to sense gas based on the influenced electrical property(ies) of the FET channel-gate coupling.

16 Claims, 7 Drawing Sheets

(58) Field of Classification Search
USPC ...................................... 422/98, 19; 436/144
See application file for complete search history.

(56) References Cited

U.S. PATENT DOCUMENTS

| | | | | |
|---|---|---|---|---|
| 4,514,263 | A * | 4/1985 | Janata | G01N 27/4143<br>257/253 |
| 4,671,852 | A * | 6/1987 | Pyke | C23F 1/38<br>257/253 |
| 5,385,865 | A * | 1/1995 | Nieder | H10D 30/014<br>257/E27.012 |
| 5,576,563 | A * | 11/1996 | Chung | G01N 27/4143<br>257/469 |
| 5,747,839 | A * | 5/1998 | Hammond | G01N 27/414<br>257/253 |
| 5,786,235 | A * | 7/1998 | Eisele | G01N 27/4143<br>438/53 |
| 7,553,458 | B2 * | 6/2009 | Fleischer | G01N 33/0047<br>422/417 |
| 9,134,270 | B2 * | 9/2015 | Blauw | G01N 27/4146 |
| 9,228,973 | B2 | 1/2016 | Usagawa | |
| 2004/0007740 | A1 * | 1/2004 | Abstreiter | G01N 27/4145<br>257/347 |
| 2004/0051150 | A1 * | 3/2004 | Wu | H10D 30/673<br>257/E29.022 |
| 2005/0079659 | A1 * | 4/2005 | Duan | H10D 62/40<br>438/197 |
| 2005/0181587 | A1 * | 8/2005 | Duan | H10K 85/221<br>438/551 |
| 2005/0212014 | A1 * | 9/2005 | Horibe | B82Y 10/00<br>257/213 |
| 2005/0212531 | A1 | 9/2005 | Wei | |
| 2006/0260737 | A1 * | 11/2006 | Fleischer | G01N 27/002<br>156/292 |
| 2006/0263255 | A1 | 11/2006 | Han et al. | |
| 2008/0063566 | A1 * | 3/2008 | Matsumoto | G01N 27/4146<br>422/50 |
| 2008/0134759 | A1 * | 6/2008 | Mohammed-Brahim | G01N 27/4143<br>257/253 |
| 2008/0197384 | A1 * | 8/2008 | Hartwich | H10D 30/6744<br>257/E21.415 |
| 2008/0237654 | A1 * | 10/2008 | Lehmann | G01N 27/4143<br>257/253 |
| 2008/0283939 | A1 | 11/2008 | Choi et al. | |
| 2009/0057660 | A1 * | 3/2009 | Bonfiglio | H10K 10/464<br>257/E51.001 |
| 2009/0194828 | A1 * | 8/2009 | Cobianu | G01P 1/023<br>257/467 |
| 2011/0146382 | A1 * | 6/2011 | Fleischer | G01N 27/4143<br>73/29.02 |
| 2011/0163353 | A1 * | 7/2011 | Senft | G01N 27/4143<br>257/253 |
| 2011/0169057 | A1 * | 7/2011 | Tsukada | G01N 27/4148<br>257/253 |
| 2011/0193164 | A1 * | 8/2011 | Zhu | H10D 30/62<br>438/151 |
| 2012/0038006 | A1 * | 2/2012 | Zhu | H10D 30/62<br>257/E21.409 |
| 2012/0280292 | A1 * | 11/2012 | Bjoerk | H10D 30/6715<br>257/E21.409 |
| 2013/0161642 | A1 * | 6/2013 | Zhu | H10D 62/021<br>257/77 |
| 2013/0186178 | A1 * | 7/2013 | Usagawa | B82Y 30/00<br>73/31.06 |
| 2014/0035007 | A1 * | 2/2014 | Krauss | G01N 27/4141<br>257/253 |
| 2014/0070170 | A1 * | 3/2014 | Andersson | G01N 27/4146<br>257/29 |
| 2014/0243214 | A1 * | 8/2014 | Haga | G01N 33/48721<br>257/253 |
| 2015/0097193 | A1 * | 4/2015 | Yap | H10D 62/121<br>257/104 |
| 2015/0125872 | A1 * | 5/2015 | Chen | G01N 27/4145<br>435/7.1 |
| 2015/0260769 | A1 * | 9/2015 | Mentzel | G01R 19/0092<br>324/713 |
| 2015/0323482 | A1 | 11/2015 | Shimoyama | |
| 2016/0003770 | A1 | 1/2016 | Klootwijk et al. | |
| 2016/0116434 | A1 * | 4/2016 | Mwakikunga | G01N 27/4141<br>257/253 |
| 2018/0130878 | A1 * | 5/2018 | Pawlak | H10D 30/6735 |
| 2018/0186623 | A1 | 7/2018 | Vossough et al. | |
| 2018/0372678 | A1 * | 12/2018 | Patolsky | G01N 27/4145 |
| 2019/0376926 | A1 * | 12/2019 | Tarasov | G01N 27/4146 |
| 2021/0013316 | A1 | 1/2021 | Asai et al. | |
| 2023/0324330 | A1 * | 10/2023 | Pascual Garcia | G01N 27/414<br>257/253 |

FOREIGN PATENT DOCUMENTS

| | | | | |
|---|---|---|---|---|
| EP | 1103809 | A1 * | 5/2001 | G01N 27/4143 |
| EP | 2705357 | B1 | 12/2016 | |
| GB | 2523173 | A | 8/2015 | |
| WO | WO-2013/128456 | A1 | 9/2013 | |
| WO | WO-2014/191892 | A1 | 12/2014 | |

OTHER PUBLICATIONS

Wu, C.-C. et al, Journal of the Electrochemical Society 2018, 165. B576-B581. (Year: 2018).*
Gaspar, D. et al, Advanced Electronic Materials 2018, 4, paper 1800423, 8 pages with 8 pages of supporting information. (Year: 2018).*
Erine, C. et al, IEEE Electron Device Letters 2020, 41, 321-324. (Year: 2020).*
Nieder, J et al, Applied Physics Letters 1990, 57, 2695-2697. (Year: 1990).*
Meiners, U. et al, Solid-State Electronics 1994, 1001-1004. (Year: 1994).*
Cha, S. N. et al, Applied Physics Letters 2006, 89, article 263102, 3 pages. (Year: 2006).*
Kettle, J. et al, Nanotechnology 2010, 21, article 075301, 7 pages. (Year: 2010).*
Zou, X. et al, Nano Letters 2013, 13, 3287-3292 with 4 pages of supporting information. (Year: 2013).*
Ahn, J.-H. et al, Applied Physics Letters 2014, 104, article 013508, 5 pages. (Year: 2014).*
Sarkar, D. et al, Nano Letters 2015, 15, 2852-2862 with 5 pages of supporting information. (Year: 2015).*
Choi, B. et al, Solid-State Electronics 2015, 114, 76-79. (Year: 2015).*
Chang, L.-C. et al, Compound Semiconductor Week (CSW) [Includes 28th International Conference on Indium Phosphide & Related Materials (IPRM) & 43rd International Symposium on Compound Semiconductors (ISCS)] 2016, 1-2. (Year: 2016).*
Pyo, J.-Y. et al, Sensors & Actuators: B. Chemical 2018, 276, 101-106. (Year: 2018).*
Nugroho, F. A. A. et al, Nature Materials 2019, 18, 489-495 with 52 pages of supplementary information. (Year: 2019).*
Hong, J. et al, ACS Applied Materials & Interfaces 2015, 7, 3554-3561 with 4 pages of supporting information. (Year: 2015).*
Ohodnicki, P. R. et al, Sensors and Actuators B 2015, 214, 159-168. (Year: 2015).*
Alwan, A. M. et al, Solid State Electronics 2019, 153, 37-45. (Year: 2019).*
Koo, W.-T. et al, Chem 2020, 6, 2746-2758 with 34 pages of supplemental information. (Year: 2020).*
Kang, et al., "Design of a Vertically Movable Gate Field Effect Transistor (VMGFET) Sensor for Low Frequency Applications", Proceedings of the International Conference of Control, Dynamic Systems, and Robotics, Ottawa, Ontario, Canada, May 15-16, 2014, Paper No. 121, 7 pages.
Zhang, et al., "On-chip surface modified nanostructured ZnO as functional pH sennsors", IOP Publishing, Nanotechnology 26 (2015) 355202 (9pp), 11 pages.

(56) References Cited

OTHER PUBLICATIONS

Kohl, "Function and applications of gas sensors", Institute of Physics Publishing, J. Phys. D: Appl. Phys. 34 (2001) R125-R149, 26 pages.
Ghosh, et al., "High-Temperature Gas Sensors for Harsh Environment Applications: A Review", Clean-Soil, Air, Water 2019, 47, 1800491, 16 pages.
Li, et al., "Chemical and Biomolecule Sensing with Organic Field-Effect Transistors", Chem. Rev. 2019, 119, 1, 3-35, https://doi.org/10.1021/acs.chemrev.8b00016, Published Nov. 7, 2018, 87 pages.
Rahman, et al., "Effect of biomolecule position and fill in factor on sensitivity of a Dielectric Modulated Double Gate Junctionless MOSFET biosensor", Sensing and Bio-Sensing Research 13 (2017) 49-54, 6 pages.
Mahfoz-Kotb, et al., "Sensing sensibility of surface micromachined suspended gate polysilicon thin film transistors", Sensors and Actuators B 118 (2006) 243-248, 6 pages.
International Search Report for PCT application PCT/EP2023/066011 dated Sep. 13, 2023.
International Preliminary Report on Patentability for PCT application PCT/EP2023/066011 mailed Sep. 26, 2024.

* cited by examiner

FET GAS SENSOR DEVICE WITH A SPACE BETWEEN A GATE AND A SEMICONDUCTOR CHANNEL HAVING AN EMBEDDED METAL NANOPARTICLE LAYER THEREON

FIELD OF THE INVENTION

The present invention relates to a field effect transistor (FET) gas sensor device.

BACKGROUND OF THE INVENTION

Field-effect transistors (FETs) may be used, among other things, in determining gas components in gas mixtures. For example, a gate electrode of the FET may react to gas components, thereby triggering a change in a control voltage applied to the gate electrode. The occurring change in the current flow resulting between the source electrode and the drain electrode may be detected and associated with the concentration of a gas component.

FET sensors of this kind can be used to detect atoms, molecules and ions in gases. Such sensors for gas analysis were first presented by Lundström (I. Lundström, S. Shivaraman, C. Svensson and L. Lundkvist, A hydrogen-sensitive MOS field effect transistor, Appl. Phys. Lett. 26, 55 (1975)). In this study, a metal oxide semiconductor FET (MOSFET) was used to detect hydrogen.

However, it should be noted that a common problem with the use of FETs for gas sensing is that the common architecture or structure of the FETs may lead to a limited sensitivity of sensing gas.

Hence, it is an object of the present invention to provide a FET-type sensor which is able to provide an increased sensitivity, response time, accuracy, and/or specificity related to gas sensing.

SUMMARY OF THE INVENTION

It is of interest to provide alternatives to the FET-type gas sensors of the prior art in order to improve the sensitivity, response time, accuracy, and/or specificity of these gas sensors.

This and other objects are achieved by providing FET gas sensor device and a method having the features in the independent claims. Preferred embodiments are defined in the dependent claims.

Hence, according to a first aspect of the present invention, there is provided a field effect transistor, FET, gas sensor device arranged to sense gas. The FET gas sensor device comprises at least one gate, a source, a drain, and a semiconductor channel arranged between the source and the drain. The semiconductor channel and the at least one gate form a FET channel-gate coupling by which an applied gate potential is arranged to control a current flowing through the semiconductor channel. The FET gas sensor further comprises at least one space arranged between the at least one gate and the semiconductor channel. The at least one space is configured to receive gas, whereby gas, received in the at least one space, is arranged to influence at least one electrical property of the FET channel-gate coupling, and wherein the FET gas sensor device is arranged to sense gas based on the influenced at least one electrical property of the FET channel-gate coupling.

According to the second aspect of the present invention, there is provided a method of sensing gas by a field effect transistor, FET, gas sensor device. The FET gas sensor device comprises at least one gate, a source, a drain, and a semiconductor channel arranged between the source and the drain, wherein the semiconductor channel and the at least one gate form a FET channel-gate coupling by which a gate potential is arranged to control a current through the semiconductor channel. The FET gas sensor further comprises at least one space arranged between the at least one gate and the semiconductor channel. The method comprises biasing the source and the drain with a first voltage for generating a current flowing through the semiconductor channel. The method further comprises biasing the gate with a second voltage and controlling the current flowing through the semiconductor channel via a FET channel-gate coupling formed by the semiconductor and the at least one gate. The method further comprises receiving gas in the at least one space, whereby gas, received in the at least one space, is arranged to influence at least one electrical property of the FET channel-gate coupling. The method further comprises sensing gas based on the influenced at least one electrical property of the FET channel-gate coupling.

Thus, the present invention is based on the concept or idea of providing a FET gas sensor device comprising one or more gas-receiving spaces between the gate(s) and the semiconductor channel, so that the space(s) is (are) directly coupled to the FET channel-gate coupling. By the arrangement of the gas-receiving space(s) between the gate(s) and the semiconductor channel, a gas to be sensed may be received or injected between the gate(s) and the semiconductor channel during the sensing. The presence of the gas between the gate(s) and the semiconductor channel in the space(s) as provided enhances the ability of the semiconductor channel of the FET gas sensor device to respond to the gas. In other words, the gas as received in the space(s) interacts with and/or couples to the FET channel-gate coupling. Consequently, the FET gas sensor device improves the sensitivity, response time, accuracy, and/or specificity of the gas sensing.

The present invention is advantageous in that the arrangement of the gate(s) and the semiconductor channel in a same (common) plane (e.g. on the same side (surface) of a substrate) leads to an effective response of the FET gas sensor device to the gas received in the space(s) between the gate(s) and the semiconductor channel. As the space(s) is (are) directly coupled to the FET channel-gate coupling, the present invention is much more efficient in its gas-sensing ability compared to prior art FET sensor, and in particular prior art FET sensors of back-gate type, wherein a gate and a semiconductor channel are arranged in different planes (e.g. on opposite sides (surfaces) of a substrate). It has been observed that these kind of FET sensors have a relatively weak capacitive coupling to the semiconductor channel. In sharp contrast, the arrangement of the FET gas sensor device of the present invention achieves a strong coupling to the FET channel-gate coupling. The architecture or structure of the FET gas sensor device of the present invention enables a direct coupling and/or transduction to the semiconductor channel, which greatly enhances the gas-sensitivity of the FET gas sensor device.

The present invention is further advantageous in that the structure and/or arrangement of the FET gas sensor device has a high transconductance, miniaturization and/or low-energy consumption.

There is provided a field effect transistor, FET, gas sensor device arranged to sense gas. By "gas", it is here meant substantially any gas, and in particular, hydrogen gas, $H_2$. The FET gas sensor device comprises at least one gate, a source, a drain, and a semiconductor channel arranged between the source and the drain. The electric potential of the gate communicates with the channel of semiconductor material(s), and a voltage bias applied between the source and the drain biases a current to flow between the source and the drain. It will be appreciated that these FET components, and their operation, are known to the skilled person, and any further description thereof is therefore omitted. The semiconductor channel and the at least one gate form a FET channel-gate coupling by which an applied gate potential is arranged to control a current flowing through the semiconductor channel. Hence, as a biasing of the gate with a voltage changes the electric field in the semiconductor channel, the term "FET channel-gate coupling" may be described to represent a correlation between the current through the channel and the gate potential (voltage), forming the FET channel-gate coupling. The FET gas sensor device further comprises at least one space arranged between the at least one gate and the semiconductor channel. By the term "space", it is here meant a three-dimensional (3D) (air) gap, space, room, area, void, or the like, which is arranged or provided between the gate(s) and the semiconductor channel. In other words, as the gate(s) and the semiconductor are physically separated in the FET gas sensor device, space(s) are provided between the gate(s) and the semiconductor channel.

The at least one space of the FET gas sensor device is configured to receive gas. Hence, the FET gas sensor device allows for gas to enter the space(s) between the gate(s) and the semiconductor channel. Gas which is received in the at least one space is arranged to influence at least one electrical property of the FET channel-gate coupling. Hence, in case gas is received (enters) the space(s) between the gate(s) and the semiconductor channel of the FET gas sensor device, electrical property(ies) of the FET channel-gate coupling may be influenced or affected by the presence of gas in the space(s). The FET gas sensor device is arranged to sense gas based on the influenced at least one electrical property of the FET channel-gate coupling. Hence, the FET gas sensor device is arranged or configured to sense or detect (the) gas based on (as a function of) the electrical property(ies) of the FET channel-gate coupling, wherein the gas influences of affects the electrical property(ies) of the FET channel-gate coupling.

According to an embodiment of the present invention, the at least one gate, the semiconductor channel, the at least one space, and at least one of the source and the drain may be arranged in a same plane. Hence, the gate(s), the semiconductor channel, the space(s), of the FET gas sensor device, as well as the source and/or the drain, are arranged in the same (common) plane. The arrangement of the FET gas sensor device components in the same, common plane leads to a particularly effective response of the FET gas sensor device to the gas received in the space(s) between the gate(s) and the semiconductor channel. This architecture or structure of the FET gas sensor device of the present invention enables a direct coupling and/or transduction to the semiconductor channel, which greatly enhances the gas-sensitivity of the FET gas sensor device. Hence, the source, the drain and the channel are arranged in a coplanar configuration. Also, at least one gate, at least one airgap and the channel are arranged in a coplanar configuration. Preferably, at least one gate, a space, the channel, and at least one of the source or the drain are arranged in a coplanar configuration. Preferably, the at least one gate, the space, the channel, the source and the gate are arranged in a coplanar configuration. Thus, the at least one gate, the space, the channel, the source and the gate are arranged in a common plane. Preferably, two gates, two spaces, the channel, the source and the gate are arranged in a coplanar configuration. Thus, the two gates, the two spaces, the channel, the source and the gate are arranged in a common plane.

According to an embodiment of the present invention, the FET gas sensor device further comprises a substrate, wherein the at least one gate, the semiconductor channel, the at least one space, and at least one of the source and the drain are arranged in a common plane parallel to a surface of the substrate. The arrangement of the FET gas sensor device components in the same, common plane parallel to the surface of the substrate allows a very efficient fabrication of the device, needing fewer fabrication steps. Such arrangement also provides the possibility to define the size of the space(s) in the processing of the FET gas sensor device, wherein the size of the space(s) preferably is ≤500 nm, being particularly suitable for gas-sensing purposes.

According to an embodiment of the present invention, the FET gas sensor device may further comprise at least one layer provided on at least a portion of the semiconductor channel, wherein the at least one layer comprises a first layer arranged to interact with gas received in the at least one space. By the term "layer", it is here meant a (relatively thin) layer, coating, cover, film, or the like. Hence, the FET gas sensor may comprise one or more layers, coatings, covers and/or films provided on at least a portion of the semiconductor channel. The present embodiment is advantageous in that the layer(s) may ameliorate one or more gas-sensing properties of the FET gas sensor device.

The at least one layer may comprise a first layer arranged to interact with gas received in the at least one space. In other words, the first layer (which also may be denoted sensing layer) is configured or arranged to interact with gas received in the space(s). The first (sensing) layer hereby interfaces gas received in the at least one space between the gate(s) and the semiconductor channel. Gas received in the space(s) may interact with the first layer, and the gas may thereby influence at least one electrical property of the FET channel-gate coupling. In other words, the interaction between the first layer and the gas couple to the FET channel-gate coupling, and hereby modulates a potential (voltage) sensed by semiconductor channel, emanating from the gate(s). Gas received or injected into the space(s) interacts with the first layer and is able to vary electrical property(ies) of the FET channel-gate coupling. Consequently, the FET gas sensor device is arranged to sense gas based on the influenced electrical property(ies) of the FET channel-gate coupling, whereby this effect is enhanced by the first layer. According to an example, the first layer may be configured for an enhanced interaction with one or more target compound(s) in the gas (relative to other constituents of the gas). It should be noted that a differentiated interaction of a first layer with various specific target compounds may allow an even more specific sensing or detection of (a) target compound(s).

According to an embodiment of the present invention, the at least one layer comprises a portion provided on a surface of the semiconductor channel facing a gate. Arranging the first layer on a surface of the channel facing a gate may increase the coupling between the gate, sensing layer and semiconductor channel giving increased sensitivity. In one embodiment the side surface of the semiconductor channel faces the gate, and the first layer is arranged on the side surface. Hence, the first layer is arranged in between the gate/space and the semiconductor channel, allowing a direct coupling.

According to an example of the present invention, the at least one layer comprises a first portion provided on a surface of the channel facing one gate, and a second portion provided on a surface of the channel facing a second gate. According to one example the first layer comprises portion(s) provided on a surface(s) of the channel, that is coplanar with the gate(s), the space(s), the channel, the source and the drain.

According to an embodiment of the present invention, the first layer may comprise at least one metal. Hence, the first layer may comprise, or even consist, of one or more metals. The present embodiment is advantageous in that the metallic first layer may even further enhance the gas sensitivity of the FET gas sensor device.

According to an embodiment of the present invention, the first layer comprises one of a film of at least one metal, metal nanoparticles (NPs), and nanoparticles of at least one metal selected from the group consisting of platinum, Pt, palladium, Pd, gold, Au, and nickel, Ni. Hence, the first layer may comprise or constitute a (relatively thin) film of one or more metals, or the first layer may comprise nanoparticles of metal(s) of platinum, Pt, palladium, Pd, gold, Au, and/or nickel, Ni. By “nanoparticles”, it is meant particles with small dimensions, of the order of less than 100 nm, and preferably less than 20 nm. The present embodiment is advantageous in that the metallic film or the nanoparticles of the first layer are particularly suitable for the gas sensitivity of the FET gas sensor device. The nanoparticles may be designed with a desired size, which allow enhanced interactions with specific gas substances. The present embodiment is particularly advantageous in that nanoparticles of the mentioned metals work as catalysts for molecular hydrogen, $H_2$, to react and penetrate the first layer towards the interface of the sensing layer to the semiconductor channel. The nanoparticles may comprise alloy or oxide nanoparticles.

According to an embodiment of the present invention, the at least one layer may comprise a second layer arranged on at least a portion of the first layer, wherein the second layer comprises at least one polymer and is arranged to protect the first layer from humidity. Hence, the FET gas sensor may comprise a second layer which comprises or consists of one or more polymers, and wherein this second layer is arranged at least partially on the first layer in order to protect the first layer from humidity.

According to an embodiment of the present invention, the at least one layer may comprise a third layer, wherein the third layer is dielectric and is arranged to passivate a surface of the semiconductor channel. Hence, the FET gas sensor may comprise a third dielectric layer which is configured or arranged to passivate a surface of the semiconductor channel. By the term “passivate”, it is here meant protect, shield, or the like. The third layer, which also may be denoted barrier layer, may be configured to protect the semiconductor channel from being deteriorated by the gas. According to an example, the third (barrier) layer may comprise, or even constitute, an oxide. According to an example, third layer may comprise at least one of an oxide (e.g. silicon dioxide, $SiO_2$, hafnium oxide, $HfO_x$, aluminum oxide, $AlO_x$) and nitride. The third layer may for example be an electric insulator.

According to an embodiment of the present invention, the third layer may be provided on at least a portion of the semiconductor channel, and the first layer may be arranged on at least a portion of the third layer. Hence, the third (barrier) layer is disposed onto the semiconductor channel, and the first (sensing) layer is disposed onto the third (barrier) layer. According to an example, the third layer may include the first layer.

According to an embodiment of the present invention, the third layer may have a thickness in the range of 0.5 nm-10 nm. Hence, the third layer may be relatively thin. Having a space, or distance between gate and semiconductor channel, e.g. less than 500 nm, may ensure that the main conducting channel is generated in the side surface of the semiconductor channel or nanowire, which is separated from the first layer only by the third layer. The relatively thin third layer according to the present embodiment may allow tunneling of electrons through the third layer. In an example, electrons can tunnel between (metal NPs embedded in the) first layer and the semiconductor channel, thus equilibrate them. The NPs with potential energy below the Fermi-level will therefore be filled with electrons. When exposed to $H_2$ gas, e.g. Pd NPs can react with $H_2$ even at room temperature. The gas reaction will form new phase(s) in the NPs and generate interface dipoles between the NPs and the $SiO_2$, which will raise the potential energy of the NPs. As a result, some filled NPs states will be lifted above the Fermi-level, and electrons in these states will be detrapped back to the semiconductor channel to generate the current signal. The electron trapping/detrapping processes generate direct communication between the e.g. Pd NPs-$H_2$ reaction and the main conducting channel, thus enabling a very efficient signal transduction.

According to an embodiment of the present invention, the third layer may have a thickness in the range of 0.5 nm-5 nm. The present embodiment is particularly advantageous regarding the tunnelling effect as previously described, as the (very) thin third layer leads to an even more efficient signal transduction.

According to an embodiment of the present invention, the semiconductor channel may elongate along an axis, A, and wherein the FET gas sensor device comprises two gates arranged on opposite sides of the semiconductor channel, perpendicular to the axis, A. The present embodiment is advantageous in that the provision of two gates may enhance the FET channel-gate coupling, consequently leading to a higher sensitivity to gas received and/or present in the spaces between the gates and the semiconductor channel. Hence, according to this embodiment, the FET gas sensor device is thus provided with a double side-gate architecture which can even further enhance its gas sensitivity compared to a single side-gate architecture comprising a single gate. According to one embodiment of the present invention the two gates, the source, the drain, the channel and the spaces are arranged in a common plane onto, and in parallel with, the surface of the substrate.

According to an embodiment of the present invention, at least a portion of the semiconductor channel may comprise a nanowire. By the term “nanowire”, it is here meant that the semiconductor channel is in the form thin wire, which preferably is thinner than 100 nm in diameter in cross section. The present embodiment is advantageous in that the nanowire with a relatively small cross-section (i.e. a relatively small cross-sectional area of the semiconductor channel) may increase a coupling between the semiconductor channel and, if provided, the first layer. In case of the provision of a first layer, at least a portion of the first layer may be disposed onto the nanowire according to an example. Furthermore, the semiconductor channel may be a 1D nanowire (channel), wherein the 1D nanowire has a particularly strong electrical coupling with the first layer.

According to an embodiment of the present invention, the FET gas sensor device may further comprise a substrate, wherein at least one of the at least one gate, the source, the drain, and the semiconductor channel are arranged on a surface of the substrate. Hence, the gate(s), the source, the drain and/or the semiconductor channel is (are) arranged on a same surface (i.e. a same side) of the substrate. By the term substrate it is here meant a substrate for mechanical and/or electrical support of the component(s) arranged thereon. The substrate may be insulating.

According to an embodiment of the present invention, the semiconductor channel may be arranged above the surface of the substrate. Hence, the semiconductor channel may be suspended, and this arrangement may be denoted as "floating (semiconductor) channel". The present embodiment is advantageous in that the FET gas sensor device achieves an even further improved heat management. For example, in case of the provision of an insulating substrate, the heat dissipation from the semiconductor channel (e.g. in the form of a (1D) nanowire), to the insulating substrate is significantly reduced. Thereby, the heat from the Joule effect of the semiconductor channel current is accumulated in the semiconductor channel, and the semiconductor channel (and first layer if provided) are heated. This increased temperature can accelerate the reaction of the FET gas sensor device, and thus improve the sensing sensitivity and/or the response time of the FET gas sensor device.

According to an embodiment of the present invention, the FET gas sensor device may further comprise a measuring unit configured to measure the influenced at least one electrical property of the FET channel-gate coupling, and sense gas based on the measured influenced at least one electrical property of the FET channel-gate coupling. By "measuring unit", it is here meant any unit, device, arrangement, component, or the like, which is arranged or configured to measure the influenced electrical property(ies) of the FET channel-gate coupling. The present embodiment is advantageous in that the measuring unit may efficiently and accurately measure the influenced electrical property(ies) of the FET channel-gate coupling. Consequently, the FET gas sensor device may sense and/or detect gas even more efficiently and accurately.

According to an embodiment of the present invention, the measuring unit may be further configured to determine a concentration of molecular hydrogen, $H_2$, in the gas based on the influenced at least one electrical property of the FET channel-gate coupling. The present embodiment is advantageous in the ability of the FET gas sensor device to sense and/or detect molecular hydrogen, $H_2$.

According to an embodiment of the present invention, the source, the drain, and the semiconductor channel may be formed from a same layer of semiconductor material. Hence, the (structure of the) source, the drain, and the semiconductor channel of the FET gas sensor device are formed from the same (common) layer of semiconductor material. Forming the source, the drain and the channel by patterning them from a thin film of a same layer of material may allow a very efficient fabrication of the device. The forming of these FET gas sensor device components from the same semiconductor material may be performed e.g. via lithography patterning followed by dry-etching.

According to an embodiment of the present invention, the at least one space is ≤500 nm. Hence, the space(s) arranged between the at least one gate and the semiconductor channel of FET gas sensor device is smaller or equal to 500 nm.

According to an example of the present invention, the FET gas sensor device is configured to passively or actively induce a flow of gas through the at least one space of the FET gas sensor device. The FET gas sensor device may include any unit, apparatus, or the like, for driving a gas flow to and through the gas-receiving space(s). This passive or active gas flow induction may even further improve the sensing sensitivity and/or the response time of the FET gas sensor device.

According to an embodiment of the second aspect of the present invention, the method may further comprise measuring the influenced at least one electrical property of the FET channel-gate coupling, and sensing gas based on the measured influenced at least one electrical property of the FET channel-gate coupling.

According to an embodiment of the second aspect of the present invention, the method may further comprise providing a layer on at least a portion of the semiconductor channel, wherein the layer comprises one of a film of at least one metal, metal nanoparticles, and nanoparticles of at least one metal selected from the group consisting of platinum, Pt, palladium, Pd, gold, Au, and nickel, Ni. The method may further comprise measuring the current through the semiconductor channel, and determining a concentration of molecular hydrogen, $H_2$, in the gas based on the measured current.

Further objectives of, features of, and advantages with, the present invention will become apparent when studying the following detailed disclosure, the drawings and the appended claims. Those skilled in the art will realize that different features of the present invention can be combined to create embodiments other than those described in the following.

BRIEF DESCRIPTION OF THE DRAWINGS

This and other aspects of the present invention will now be described in more detail, with reference to the appended drawings showing embodiment(s) of the invention.

DETAILED DESCRIPTION

Figure 1:
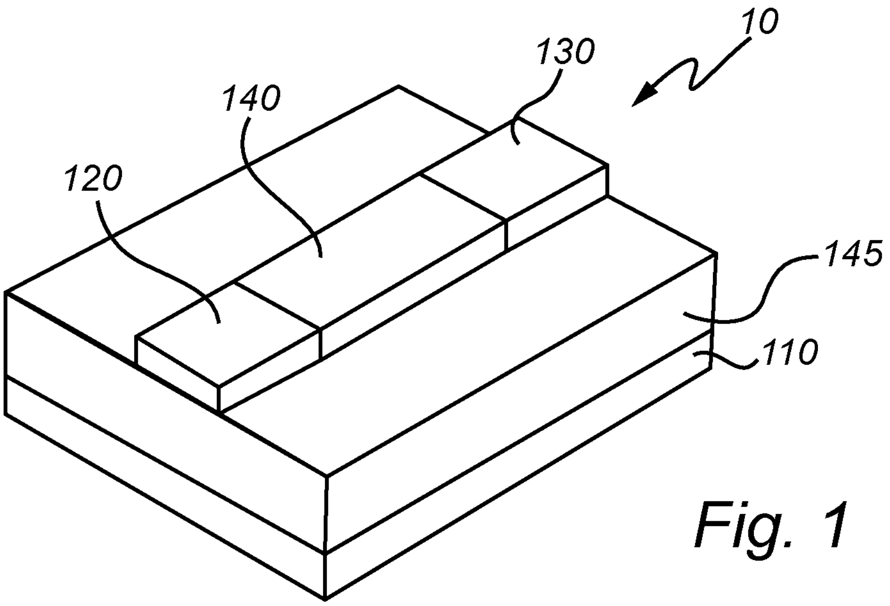
FIG. 1 schematically shows a FET gas sensor 10 according to an example of the prior art.

FIG. 1 schematically shows a FET gas sensor 10 according to an example of the prior art. Gas sensing is very important for security and environmental monitoring. Hydrogen sensing is taken as an example, but other gases could be sensed as well. Hydrogen gas is highlighted as a clean fuel because only water is produced in hydrogen combustion. Meanwhile, hydrogen gas is a flammable gas with a low explosion limit of 4% by volume in air. Hence, even a relatively low-level leakage of hydrogen gas may be a serious concern for its secure production and utilization. Thereby, a sensitive and rapid sensor for gas (hydrogen) leakage detection is of high demand, and in particular for the safety needs in the development of hydrogen energy.

FETs have been explored as a device platform for hydrogen gas sensing due to their high transconductance, miniaturization, and low-energy consumption. The prior art FET gas sensor 10 as exemplified in FIG. 1 comprises a source 120, a drain 130, and a semiconductor channel 140 arranged between the source 120 and the drain 130. The source 120, the drain 130 and the semiconductor channel 140 are arranged on an insulating substrate 145. In turn, the insulating substrate 145 is arranged on a gate 110. However, a problem with FET gas sensors 10 of this kind is the low (limited) gas sensitivity and/or detection limit. Hence, it is of interest to provide alternatives to the FET-type gas sensors of the prior art in order to improve the sensitivity, response time, accuracy, and/or specificity of these gas sensors.

Figure 2A:
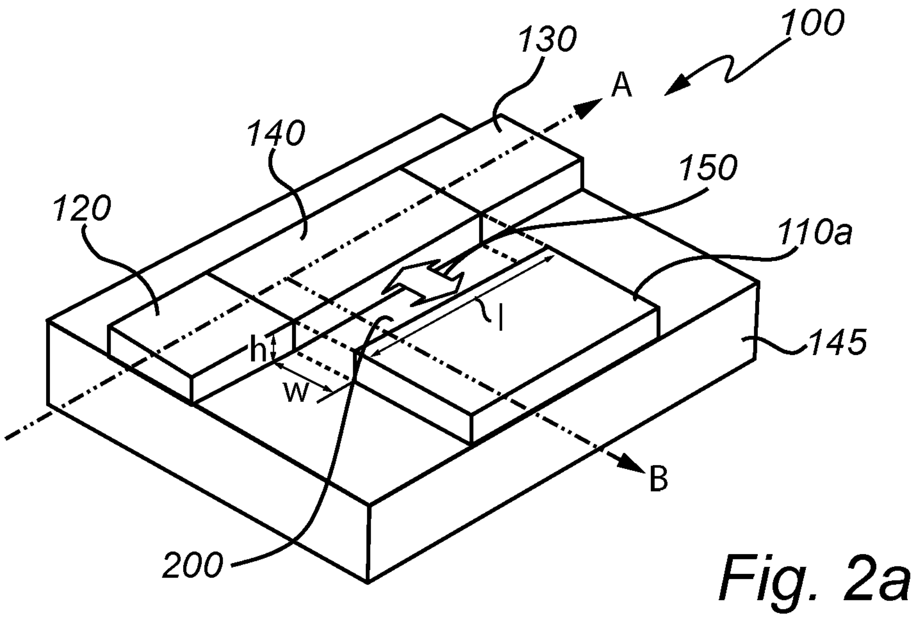
FIG. 2*a* schematically shows a FET gas sensor device according to an exemplifying embodiment of the present invention.

FIG. 2*a* schematically shows a FET gas sensor device 100 according to an exemplifying embodiment of the present invention. The FET gas sensor device 100, which in FIG. 1 may represent a side-gate FET gas sensor device, is arranged to sense gas, e.g. hydrogen gas, $H_2$. The FET gas sensor device 100 comprises at least one gate 110*a*. In FIG. 1*a*, only a single gate 110*a* is shown, but the FET gas sensor device 100 may alternatively comprise two or more gates. The FET gas sensor device 100 further comprises a source 120, a drain 130, and a semiconductor channel 140 arranged between the source 120 and the drain 130. The semiconductor channel 140 elongates along an axis, A, and as the source 120 and the drain 130 are arranged on either ends of the semiconductor channel 140, the source 120, the drain 130 and the semiconductor channel 140 form an array of components elongating along the axis, A.

According to this example of the FET gas sensor device 100, the gate 110*a*, the source 120, the drain 130 and the semiconductor channel 140 are arranged on an insulating substrate 145. The gate 110*a*, the source 120, the drain 130 and the semiconductor channel 140 are hereby arranged in a common plane. The semiconductor channel 140 and the gate 110*a* form a (schematically indicated) FET channel-gate coupling 150 by which a potential applied to the gate 110*a* is arranged to control a current flowing through the semiconductor channel 140. The FET channel-gate coupling 150 hereby represents a correlation between the current through the semiconductor channel 140 and the gate 110*a* potential (voltage), forming the FET channel-gate coupling 150.

The gate 110*a* is physically separated from the semiconductor channel 140 in a direction, B, perpendicular to the axis, A. The FET gas sensor device 100 hereby comprises at least one space 200, indicated by dashed lines, arranged between the gate 110*a* and the semiconductor channel 140. The space(s) 200 hereby constitute(s) a three-dimensional (3D) space, room, area, void, or the like, which is arranged or provided between the gate 110*a* and the semiconductor channel 140. Hence, the gate 110*a* is spaced apart from the semiconductor channel 140, forming a gap between the gate 110*a* and the semiconductor channel 140, whereby the gap is not occupied by solid material. The gap forms the gas-receiving space(s) 200 for receiving gas to be sensed. The space(s) 200 may be open to the environment to allow gas communication with the environment. Thus, gas present in the gas-receiving space(s) 200 can be replaced with new gas from the environment.

The width, w, of the space(s) 200 may be defined by the arrangement of the gate 110*a* from the semiconductor channel 140, i.e. the distance between the gate 110*a* and the semiconductor channel 140 parallel to the direction, B. The length, l, of the space(s) 200 may be defined by the length of the gate 110*a* and/or the semiconductor channel 140 parallel to the axis, A. The height, h, of the space(s) 200 may be defined by the height of the gate 110*a* and/or semiconductor channel 140 perpendicular to the axis, A, and perpendicular to the direction, B. According to the example of the FET gas sensor device 100 of FIG. 1, the space 200 provided between the gate 110*a* and the semiconductor channel 140, has a parallelepiped shape as indicated by the dashed lines.

The space 200 is configured to receive gas in that the FET gas sensor device 100 allows for gas to enter the space 200 between the gate 110*a* and the semiconductor channel 140. Gas which is received in the space 200 is arranged to influence at least one electrical property of the FET channel-gate coupling 150. The FET gas sensor device 100 is arranged to sense gas based on the influenced at least one electrical property of the FET channel-gate coupling 150. Hence, the FET gas sensor device 100 is arranged or configured to sense or detect (the) gas based on (as a function of) the electrical property(ies) of the FET channel-gate coupling 150, wherein the gas influences of affects the electrical property(ies) of the FET channel-gate coupling 150.

Figure 2B:
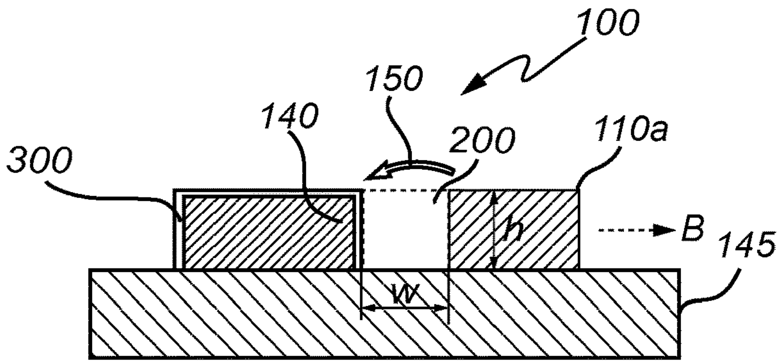
FIGS. 2*b-e* schematically show cross sections of a FET gas sensor device according to exemplifying embodiments of the present invention.

FIG. 2*b* schematically shows a cross section of a FET gas sensor device 100, along the axis, A, according to an exemplifying embodiment of the present invention. The FET gas sensor device 100 as exemplified in FIG. 2*b* corresponds to the FET gas sensor device 100 as exemplified in FIG. 2*a*, and it is referred to FIG. 2*a* and the associated text for an increased understanding of the features and/or functioning of the FET gas sensor device 100. In FIG. 2*b*, the semiconductor channel 140 and the gate 110*a*, which are arranged on the insulating substrate 145, are arranged at distance from each other along the direction, B, perpendicular to the axis, A. The gate 110*a* and the semiconductor channel 140 thereby form a space 200 between the gate 110*a* and the semiconductor channel 140. The distance between the semiconductor channel 140 and the gate 110*a* defines the width, w, of the space(s) 200, and the height, h, of the space(s) 200 is defined by the height of the semiconductor channel 140 and/or the gate 110*a*. The space 200 is configured to receive gas, whereby gas, received in the space 200, is arranged to influence electrical property(ies) of the FET channel-gate coupling 150. The FET gas sensor device 100 is arranged to sense gas based on the influenced electrical property(ies) of the FET channel-gate coupling 150.

The FET gas sensor device 100 as exemplified in FIG. 2*b* comprises a first layer (sensing layer) 300 provided on at least a portion of the semiconductor channel 140. The first layer 300, also denoted sensing layer, is arranged to interact with gas received in the space 200. The first layer 300, which may comprise at least one metal, may further comprise or consist of a film of metal(s), or comprise nanoparticles of metal(s) selected from the group consisting of platinum, Pt, palladium, Pd, gold, Au, and nickel, Ni. One or more electrical properties of the FET channel-gate coupling 150 (e.g. the semiconductor channel 140 conductance) is modulated with the gate 110*a*, and the first layer 300 is directly coupled to the semiconductor channel 140. The FET channel-gate coupling 150 is enhanced due to the first layer 300 being located between the semiconductor channel 140 and the gate 110*a*. According to one example, the presence of the gas in the gas-receiving space(s) 200 may influence the surface charge density of the first layer 300 and may influence the conduction properties of the semiconductor channel 140. According to the example of FIG. 2*b*, at least a portion of the first layer 300 is arranged in between the gate 110*a* and the semiconductor channel 140. One interaction mechanism may involve adsorption or absorption of a compound on or in the first layer 300 and change the charge distribution in layers on the semiconductor channel 140. The changes in charge distribution may be transduced to a potential signal seen by the semiconductor channel 140. According to an example, the first layer 300 may be disposed as a lining configured to at least partially enclose the space(s) 200. According to an example, at least a portion of the layer 300 is provided on a side surface of the channel. According to an example, at least a portion of the layer 300 is provided on a surface of the channel facing the space and the gate. According to another example, the first layer 300 is disposed so that it is in gas communication with gas present in the gas-receiving space 200. The minimum distance between the surface of the first layer 300 and the surface of the gate 110*a* is equal to or less than 500 nm. In the example of FIG. 2*b*, this distance is 5-100 nm, as this dimension is particularly suitable for gas-sensing purposes.

Figure 2C:
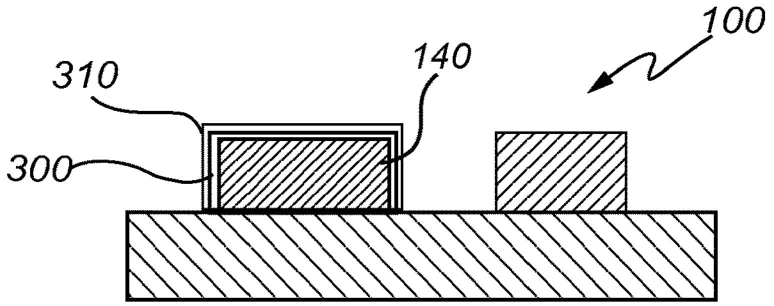

FIG. 2*c* schematically shows a cross section of a FET gas sensor device 100 according to an exemplifying embodiment of the present invention. The FET gas sensor device 100 as exemplified in FIG. 2*c* corresponds to the FET gas sensor device 100 as exemplified in FIG. 2*b*, and it is referred to FIG. 2*b* and the associated text for an increased understanding of the features and/or functioning of the FET gas sensor device 100. Compared to the FET gas sensor device 100 shown in FIG. 2*b*, the FET gas sensor device 100 shown in FIG. 2*c* further comprises a second layer 310 arranged on at least a portion of the first layer 300. Hence, the first layer 300 is provided on at least a portion of the semiconductor channel 140, and the second layer 310 is arranged on at least a portion of the first layer 300. The second layer 310 comprises at least one polymer and is arranged to protect the first layer 300 from humidity.

Figure 2D:
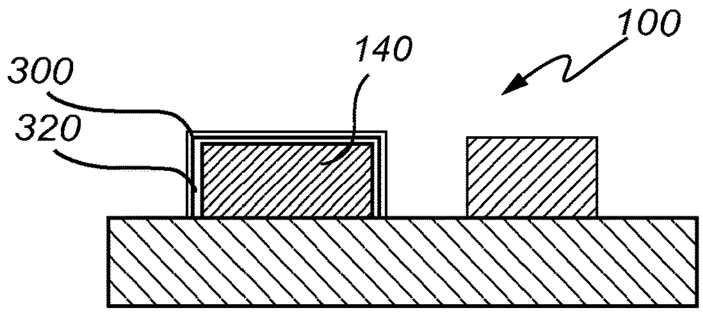

FIG. 2*d* schematically shows a cross section of a FET gas sensor device 100 according to an exemplifying embodiment of the present invention. Compared to the FET gas sensor device 100 shown in FIG. 2*b*, the FET gas sensor device 100 shown in FIG. 2*d* further comprises a third layer 320 provided on at least a portion of the semiconductor channel 140. The third layer 320, also denoted barrier layer or passivation layer, of the FET gas sensor device 100, is dielectric and is arranged to passivate a surface of the semiconductor channel 140. The third layer 320 is provided on at least a portion of the semiconductor channel 140, and the first layer 300 is arranged on at least a portion of the third layer 320. According to one example, gas molecules in the space(s) 200 may form a dipole layer at the interface between the first layer 300 and the third layer 320 and may influence the electric conduction properties of the semiconductor channel 140. According to yet another example, gas introduced in the space(s) 200 may interact with the traps at the interface between the third (dielectric) layer 320 and the semiconductor channel 140 and may influence the electrical property(ies) of the FET channel-gate coupling 150.

Figure 2E:
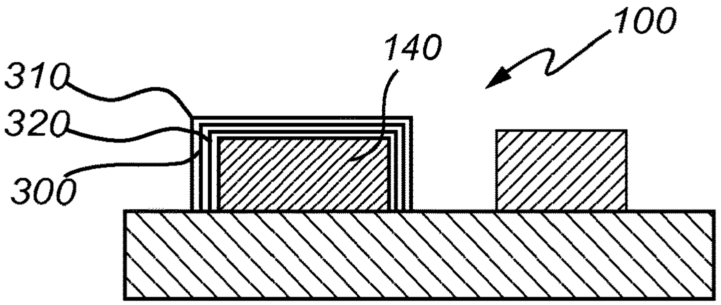

FIG. 2*e* schematically shows a cross section of a FET gas sensor device 100 according to an exemplifying embodiment of the present invention. The FET gas sensor device 100 comprises, on the semiconductor channel 140, the first layer 300 according to FIG. 2*b* and the associated text, the second layer 310 according to FIG. 2*c* and the associated text, and the third layer 320 according to FIG. 2*d* and the associated text.

Figure 3A:
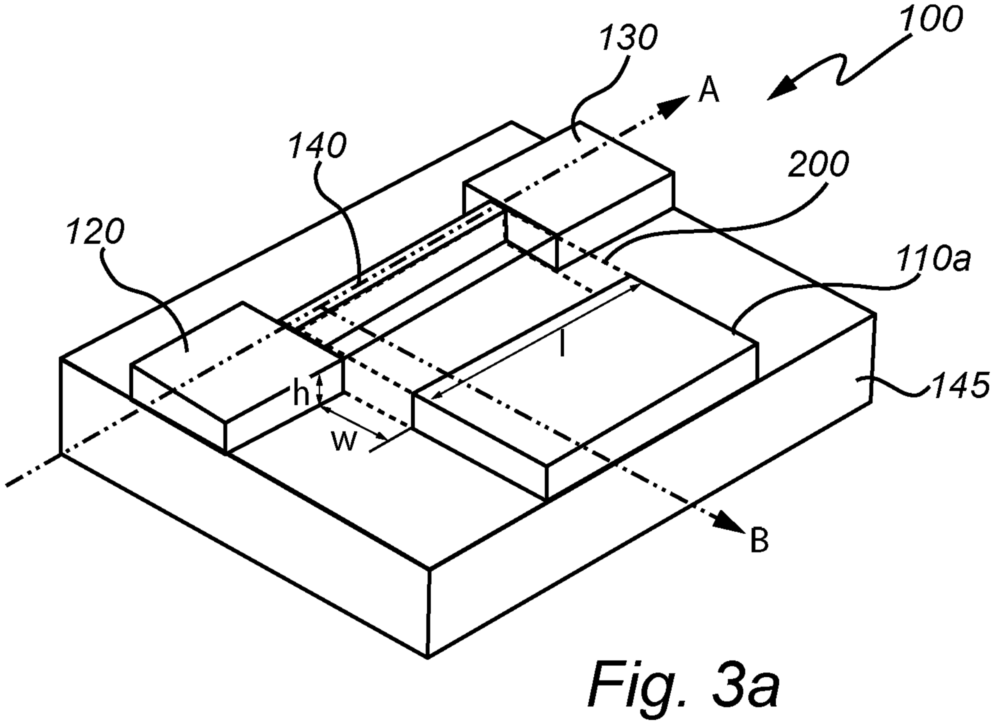
FIG. 3*a* schematically shows a FET gas sensor device according to an exemplifying embodiment of the present invention.

FIG. 3*a* schematically shows a FET gas sensor device 100 according to an exemplifying embodiment of the present invention. The FET gas sensor device 100 as exemplified in FIG. 3*a* corresponds to the FET gas sensor device 100 as exemplified in FIG. 2*a*, and it is referred to FIG. 2*a* and the associated text for an increased understanding of the features and/or functioning of the FET gas sensor device 100. In FIG. 3*a*, at least a portion of the semiconductor channel 140 comprises a nanowire. As exemplified in FIG. 3*a*, the (entire) semiconductor channel 140 constitutes a nanowire, and the nanowire may for example comprise silicone, Si. The width of the nanowire parallel to the direction, B, is smaller compared to the width of the semiconductor channel 140, as shown in FIG. 2*a*. Here, the at least one space 200, arranged or configured to receive gas, is arranged between the at least one gate 110*a* and the semiconductor channel 140 comprising the nanowire.

Figure 3B:
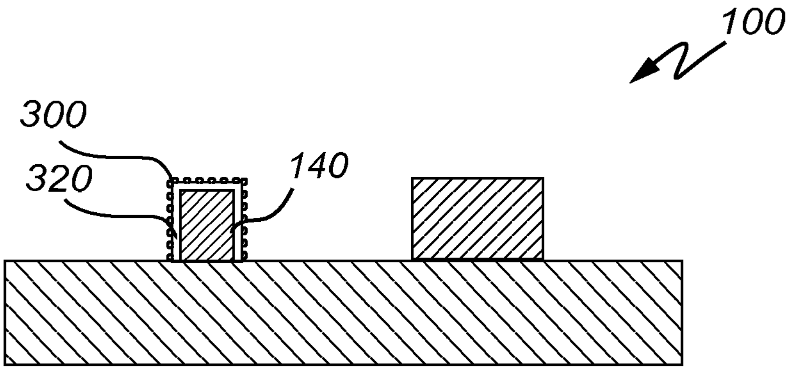
FIG. 3*b* schematically show cross sections of a FET gas sensor device according to exemplifying embodiments of the present invention.

FIG. 3*b* schematically shows a cross section of a FET gas sensor device according to an exemplifying embodiment of the present invention. The FET gas sensor device 100 as exemplified in FIG. 3*b* corresponds to the FET gas sensor device 100 as exemplified in FIG. 3*a*, and it is referred to FIG. 3*a* and the associated text for an increased understanding of the features and/or functioning of the FET gas sensor device 100. A first layer 300 is provided on at least a portion of the nanowire (semiconductor channel) 140. The first layer 300 comprises nanoparticles of metal(s), as schematically indicated by the dots, wherein the metal(s) is (are) selected from the group consisting of platinum, Pt, palladium, Pd, gold, Au, and nickel, Ni.

Figure 4A:
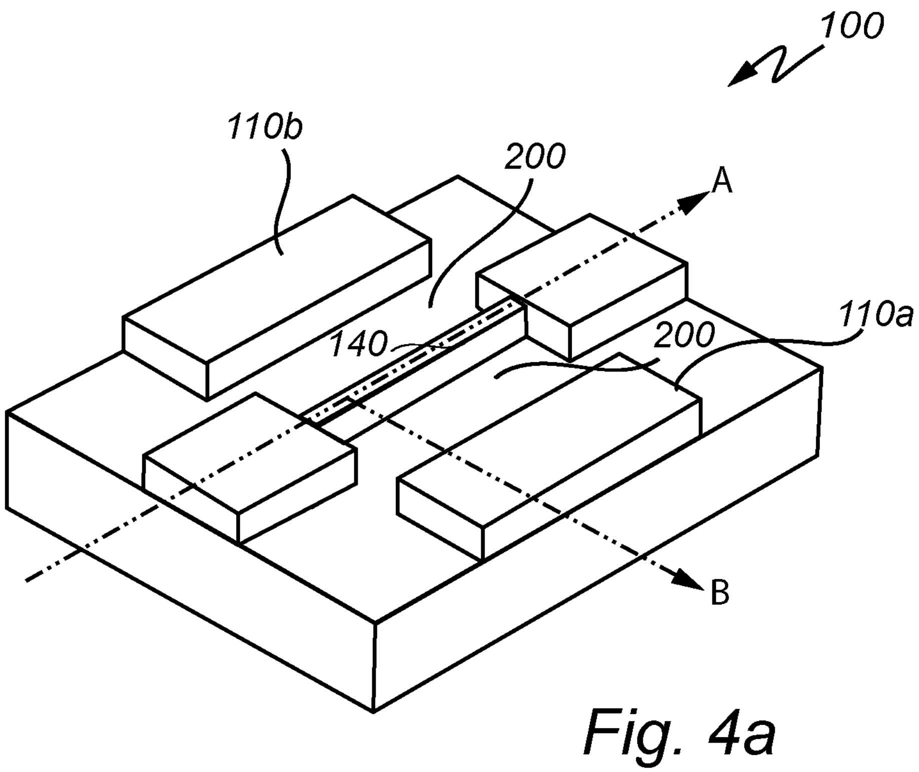
FIG. 4*a* schematically shows a FET gas sensor device according to an exemplifying embodiment of the present invention.

The FET gas sensor device 100 further comprises a third (barrier) layer 320, wherein the third layer 320 may comprise an oxide. Having a space, or distance between gate and channel, less than 500 nm, may ensure that the main conducting channel is generated in the side surface of the channel or nanowire, which is separated from the metal nanoparticles embedded in the first layer only by the third layer. In an example the oxide of the third layer is $SiO_2$ with thickness less than 10 nm. In an example the oxide of the third layer is $SiO_2$ with thickness less than 7 nm. In an example the oxide of the third layer is $SiO_2$ with thickness less than 5 nm. In an example the oxide of the third layer is $SiO_2$ with thickness less than 2 nm. In an example the oxide of the third layer is $SiO_2$ with thickness more than 0.5 nm. In an example the oxide of the third layer is $SiO_2$ with a thickness more than 1 nm. Having a thin third layer may allow tunneling of electrons through the third layer. In an example, electrons can tunnel between the metal nanoparticles embedded in the first layer and the semiconductor channel, thus equilibrate them. The NPs with potential energy below the Fermi-level will therefore be filled with electrons. When exposed to $H_2$ gas, Pd NPs can react with $H_2$ even at room temperature. The gas reaction will form new phase(s) in the NPs and generate interface dipoles between the NPs and the $SiO_2$, which will raise the potential energy of the NPs. As a result, some filled NPs states will be lifted above the Fermi-level, and electrons in these states will be detrapped back to the semiconductor channel, thus generating the current signal. The electron trapping/detrapping processes generate direct communication between the Pd NPs-$H_2$ reaction and the main conducting channel, thus enabling a very efficient signal transduction. FIG. 4*a* schematically shows a FET gas sensor device 100 according to an exemplifying embodiment of the present invention. The semiconductor channel 140 is exemplified as a (silicon, Si) nanowire according to the example of the FET gas sensor device 100 of FIG. 3*a*. The FET gas sensor device 100 comprises two gates 110*a*, 110*b* arranged on opposite sides of the semiconductor channel 140, perpendicular to the axis, A. Hence, each of the gates 110*a*, 110*b* is separated from the semiconductor channel 140 along the direction, B, perpendicular to the axis, A. Thus, compared to the FET gas sensor device 100 according to FIGS. 2*a-e*, 3*a* and/or 3*b*, disclosing (single) side gate FET gas sensor device(s) 100, the FET gas sensor device 100 in FIG. 4*a* represents a double side gate FET gas sensor device(s) 100. Here, two spaces 200 arranged or configured to receive gas are arranged on either side of the semiconductor channel 140, between the two gates 110*a*, 110*b* and the semiconductor channel 140.

Figure 4B:
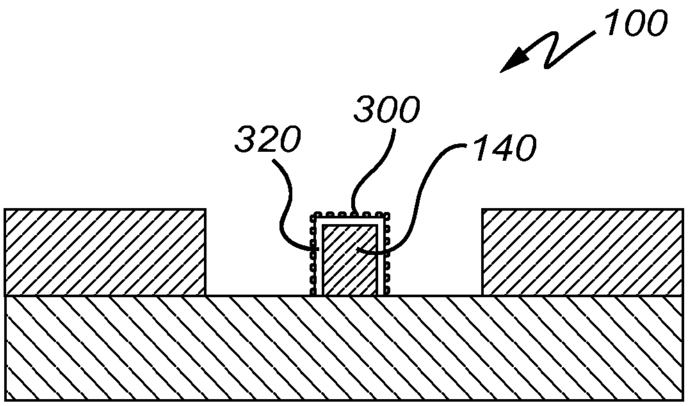
FIG. 4*b* schematically show cross sections of a FET gas sensor device according to exemplifying embodiments of the present invention.

FIG. 4*b* schematically shows a cross section of a FET gas sensor device 100 according to an exemplifying embodiment of the present invention. The FET gas sensor device 100 as exemplified in FIG. 4*b* corresponds to the FET gas sensor device 100 as exemplified in FIG. 4*a*, and it is referred to FIG. 4*a* and the associated text for an increased understanding of the features and/or functioning of the FET gas sensor device 100. A first layer 300 is provided on at least a portion of the nanowire (semiconductor channel) 140. The first layer 300 comprises nanoparticles of metal(s), as schematically indicated by the dots, wherein the metal(s) is (are) selected from the group consisting of platinum, Pt, palladium, Pd, gold, Au, and nickel, Ni. The FET gas sensor device 100 further comprises a third (barrier) layer 320, wherein the third layer 320 may comprise an oxide.

Figure 5A:
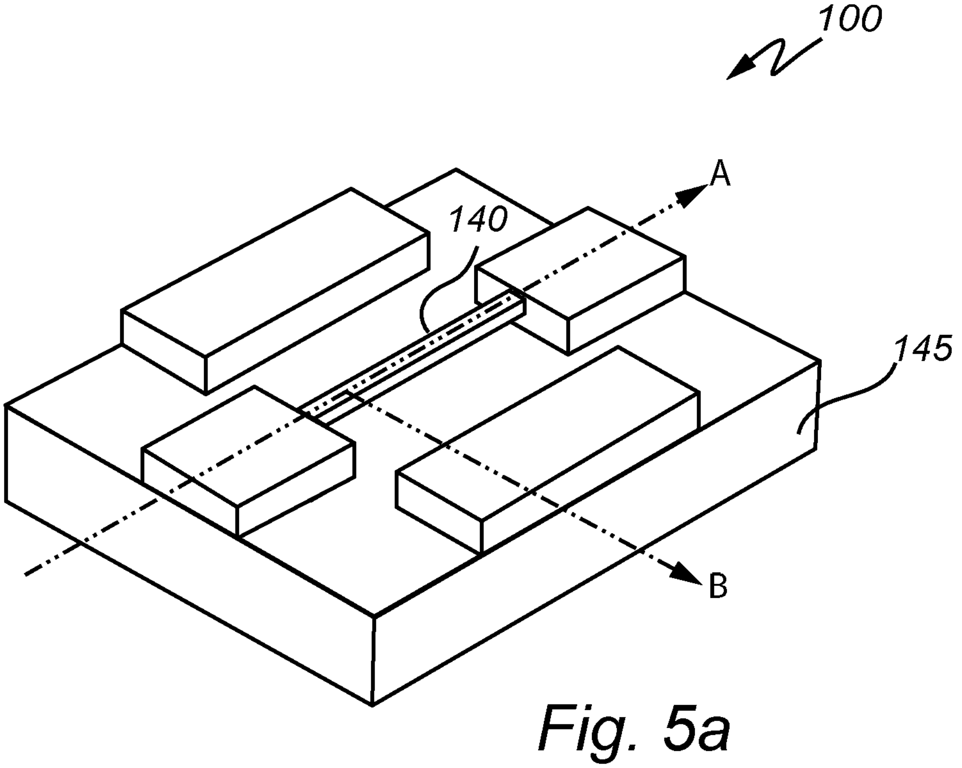
FIG. 5*a* schematically shows a FET gas sensor device according to an exemplifying embodiment of the present invention.

FIG. 5*a* schematically shows a FET gas sensor device 100 according to an exemplifying embodiment of the present invention. The FET gas sensor device 100 as exemplified in FIG. 5*a* corresponds to the FET gas sensor device 100 as exemplified in FIG. 4*a*, and it is referred to FIG. 4*a* and the associated text for an increased understanding of the features and/or functioning of the FET gas sensor device 100. Compared to FIG. 4*a*, the semiconductor channel 140 (in the form of a nanowire) is arranged above the surface of the substrate 145. Hence, the semiconductor channel 140 is suspended by the source 120 and the drain 130.

Figure 5B:
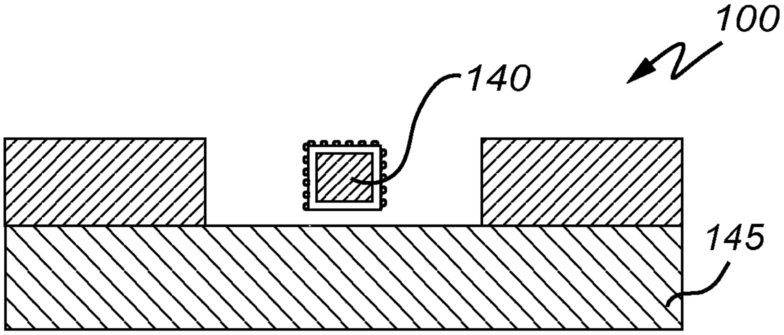
FIG. 5*b* schematically show cross sections of a FET gas sensor device according to exemplifying embodiments of the present invention.
Figure 6:
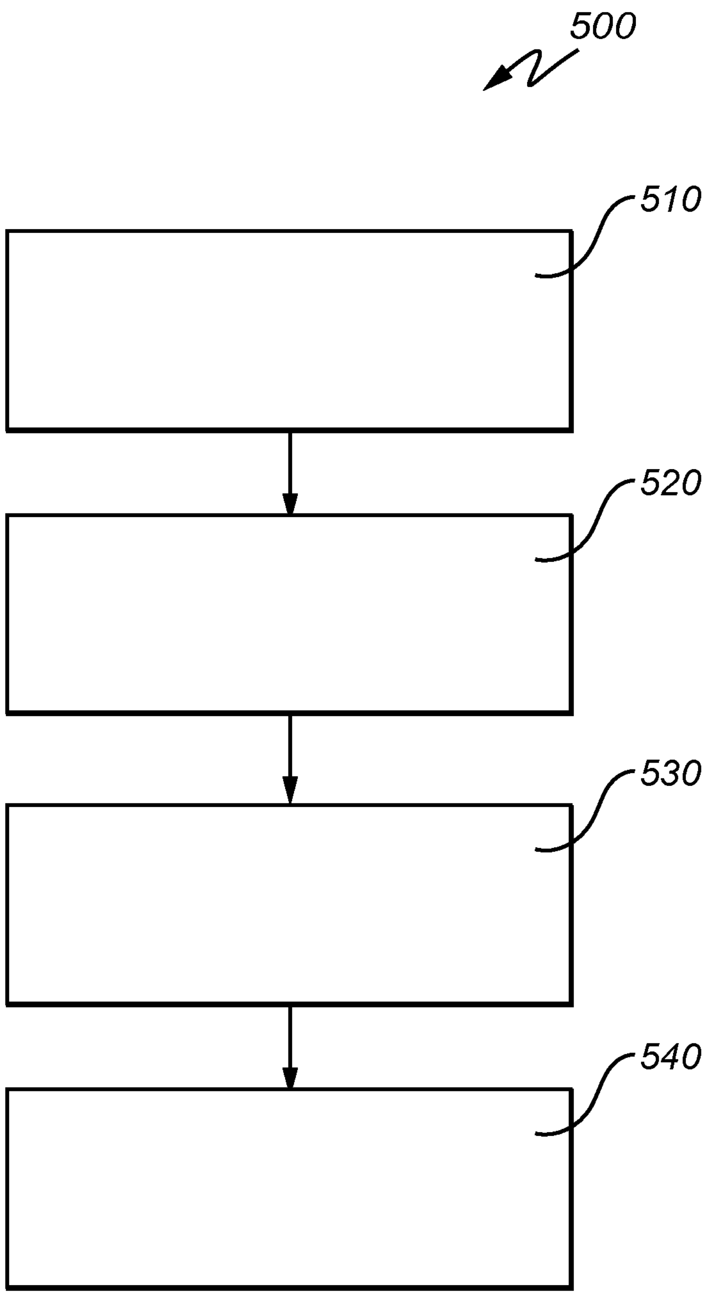
FIG. 6 schematically shows a flow chart of a method according to an exemplifying embodiment of the present invention.

FIG. 5*b* schematically shows a cross section of a FET gas sensor device 100 according to an exemplifying embodiment of the present invention, showing the suspended arrangement of the semiconductor channel 140 above the surface of the substrate 145. FIG. 6 shows a flow chart of a method 500 of sensing gas by a FET gas sensor device. The FET gas sensor device comprises at least one gate, a source, a drain, and a semiconductor channel arranged between the source and the drain, wherein the semiconductor channel and the at least one gate form a FET channel-gate coupling by which a gate potential is arranged to control a current through the semiconductor channel. The FET gas sensor further comprises at least one space arranged between the at least one gate and the semiconductor channel. The method 500 comprises the step of biasing 510 the source and the drain with a first voltage for generating a current flowing through the semiconductor channel. The method further comprises the step of biasing 520 the gate with a second voltage and controlling the current flowing through the semiconductor channel via a FET channel-gate coupling formed by the semiconductor and the at least one gate. The method further comprises the step of receiving 530 gas in the at least one space, whereby gas, received in the at least one space, is arranged to influence at least one electrical property of the FET channel-gate coupling. The method further comprises the step of sensing 540 gas based on the influenced at least one electrical property of the FET channel-gate coupling.

Figure 7A:
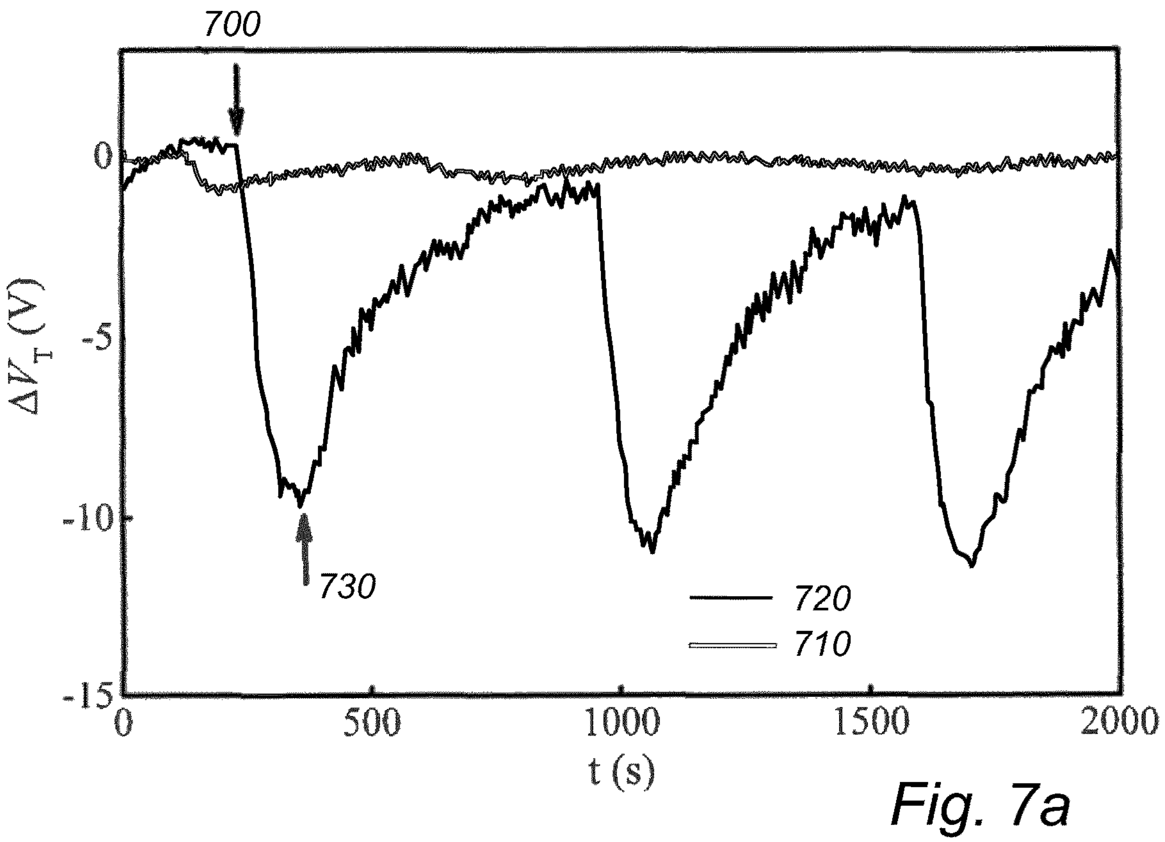
FIGS. 7*a* and 7*b* schematically show the performance of a FET gas sensor device according to exemplifying embodiments of the present invention.

FIG. 7*a* schematically shows the performance of a FET gas sensor device 100 according to an exemplifying embodiment of the present invention having a (single) side-gate FET gas sensor device 100, e.g. according to FIGS. 2*a*, 2*b*, 3*a* and/or 3*b*. In FIG. 7*a*, a comparison in voltage signal ($\Delta Vr_T(V)$) as a function of time(s) is shown between a FET sensor of the prior art (as shown in FIGS. 1*a*, 1*b*) and a FET gas sensor device 100 according to the present invention. Both the prior art FET sensor and the FET gas sensor device 100 were subjected to a regular air flow. At the location of the first arrow 700, molecular hydrogen, $H_2$, with a concentration of 2000 ppm was introduced. The voltage signal 710 of the prior art FET sensor does barely not react, while the voltage signal 720 of the FET sensor device 100 according to the invention shows significant response. At the location of the second arrow 730, air is introduced, and the graph shows the recovery behavior. The procedure is cycled several times with repeatable responses, showing significant responses to the gas for the FET gas sensor device 100 of the present invention, whereas the prior art FET sensor shows (a) minimal response(s) to the gas.

Figure 7B:
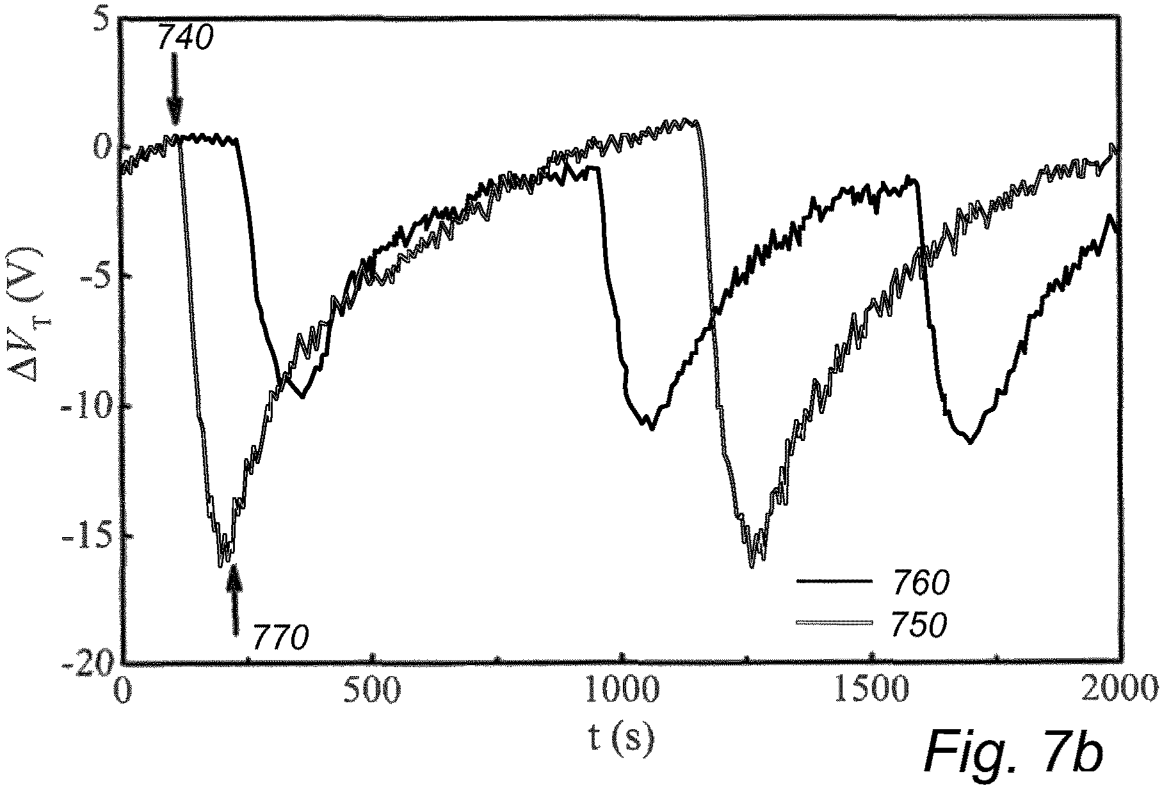

FIG. 7*b* schematically shows the performance of a FET gas sensor device 100 according to an exemplifying embodiment of the present invention having a single side-gate FET gas sensor device 100, e.g. according to FIGS. 2*a*, 2*b*, 3*a* and/or 3*b*, compared to a FET gas sensor device 100 according to an exemplifying embodiment of the present invention having a double side-gate FET gas sensor device 100, e.g. according to FIGS. 4*a*, 4*b*, 5*a* and/or 5*b*. At the location of the first arrow 740, molecular hydrogen, $H_2$, with a concentration of 2000 ppm was introduced. The voltage signal 750 of the double side-gate FET gas sensor device 100 shows a more significant response compared to voltage signal 760 the single side-gate FET gas sensor device 100. At the location of the second arrow 770, air is introduced, and the graph shows the recovery behavior. The procedure is cycled several times with repeatable responses.

The person skilled in the art realizes that the present invention by no means is limited to the preferred embodiments described above. On the contrary, many modifications and variations are possible within the scope of the appended claims. For example, one or more of the gate(s) 110*a*, 110*b*, the semiconductor channel 140, the space(s) 200, etc., may have different shapes, dimensions and/or sizes than those depicted/described.

The invention claimed is:

1. A field effect transistor, FET, gas sensor device arranged to sense gas, comprising:

at least one gate, a source, a drain, a semiconductor channel arranged between the source and the drain, wherein the semiconductor channel and the at least one gate form a FET channel-gate coupling by which an applied gate potential is arranged to control a current flowing through the semiconductor channel, at least one space arranged between the at least one gate and the semiconductor channel, wherein the at least one space is configured to receive the gas, a substrate, and at least one layer provided on at least a portion of the semiconductor channel, wherein the at least one layer comprises:

a first layer comprising metal nanoparticles embedded therein, wherein the metal nanoparticles embedded in the first layer are arranged to interact with gas received in the at least one space, and a third layer, wherein the third layer is dielectric and is arranged to passivate a surface of the semiconductor channel, wherein the third layer is provided on at least a portion of the semiconductor channel, and the first layer is arranged directly on at least a portion of the third layer, wherein the third layer has a thickness in a range of 0.5 nm-10 nm configured to allow tunnelling of electrons through the third layer between the metal nanoparticles embedded in the first layer and the semiconductor channel, wherein the metal nanoparticles are selected for having a reaction with the gas received in the at least one space to form a new phase in the metal nanoparticles, generate interface dipoles between the metal nanoparticles and the third layer, whereby a potential energy of the metal nanoparticles is changed, to allow the tunnelling of electrons through the third layer to generate a current signal in the current flowing through the semiconductor channel, wherein the first layer is directly coupled to the semiconductor channel by the allowed tunnelling of electrons through the third layer, wherein the at least one layer comprises a portion provided on a side surface of the semiconductor channel facing the at least one space configured to receive the gas and a gate of the at least one gate, wherein the at least one gate, the semiconductor channel, the at least one space configured to receive the gas, at least one of the source and the drain, and the portion of the at least one layer are arranged in a same plane parallel to a surface of the substrate, whereby the gas, received in the at least one space configured to receive the gas, is arranged to influence at least one electrical property of the FET channel-gate coupling, and wherein the FET gas sensor device is arranged to sense gas based on the influenced at least one electrical property of the FET channel-gate coupling.

2. The FET gas sensor device according to claim 1, wherein the first layer is separated from a main conducting channel, generated in a side surface of the semiconductor channel, by the third layer.

3. The FET gas sensor device according to claim 1, wherein the first layer comprises nanoparticles of at least one metal selected from the group consisting of platinum, Pt, palladium, Pd, gold, Au, and nickel, Ni.

4. The FET gas sensor device according to claim 1, wherein the at least one layer comprises a second layer arranged on at least a portion of the first layer, wherein the second layer comprises at least one polymer and is arranged to protect the first layer from humidity.

5. The FET gas sensor device according to claim 1, wherein the third layer has a thickness in the range of 0.5 nm-5 nm.

6. The FET gas sensor device according to claim 1, wherein the semiconductor channel elongates along an axis, A, and wherein the FET gas sensor device comprises two gates arranged on opposite sides of the semiconductor channel, perpendicular to the axis, A.

7. The FET gas sensor device according to claim 1, wherein at least a portion of the semiconductor channel comprises a nanowire.

8. The FET gas sensor device according to claim 1, wherein at least one of the at least one gate, the source, the drain, and the semiconductor channel are arranged on a surface of the substrate.

9. The FET gas sensor device according to claim 8, wherein the semiconductor channel is arranged above the surface of the substrate.

10. The FET gas sensor device according to claim 1, further comprising a measuring unit configured to measure the influenced at least one electrical property of the FET channel-gate coupling, and sense gas based on the measured influenced at least one electrical property of the FET channel-gate coupling.

11. The FET gas sensor device according to claim 1, wherein the source, the drain, and the semiconductor channel are formed from a same layer of semiconductor material.

12. The FET gas sensor device according to claim 1, wherein the at least one space is ≤500 nm.

13. The FET gas sensor device according to claim 12, wherein the at least one space is 5-100 nm.

14. A method of sensing gas by a field effect transistor, FET, gas sensor device comprising at least one gate, a source, a drain, a semiconductor channel arranged between the source and the drain, wherein the semiconductor channel and the at least one gate form a FET channel-gate coupling by which a gate potential is arranged to control a current through the semiconductor channel, at least one space arranged between the at least one gate and the semiconductor channel, wherein the at least one space is configured to receive the gas, and a substrate, wherein the FET gas sensor device further comprises at least one layer provided on at least a portion of the semiconductor channel, wherein the at least one layer comprises a first layer comprising metal nanoparticles embedded therein, wherein the metal nanoparticles embedded in the first layer are arranged to interact with the gas received in the at least one space, and a third layer, wherein the third layer is dielectric and is arranged to passivate a surface of the semiconductor channel, wherein the third layer is provided on at least a portion of the semiconductor channel, and the first layer is arranged directly on at least a portion of the third layer, wherein the third layer has a thickness in a range of 0.5 nm-10 nm configured to allow tunnelling of electrons through the third layer between the metal nanoparticles embedded in the first layer and the semiconductor channel, wherein the metal nanoparticles are selected for having a reaction with the gas received in the at least one space to form a new phase in the metal nanoparticles, generate interface dipoles between the metal nanoparticles and the third layer, whereby a potential energy of the metal nanoparticles is changed, to allow the tunnelling of electrons through the third layer to generate a current signal in the current flowing through the semiconductor channel, wherein the first layer is directly coupled to the semiconductor channel by the allowed tunnelling of electrons through the third layer, wherein the at least one layer comprises a portion provided on a side surface of the semiconductor channel facing the at least one space configured to receive the gas and a gate of the at least one gate, wherein the at least one gate, the semiconductor channel, the at least one space configured to receive the gas, at least one of the source and the drain, and the portion of the at least one layer are arranged in a same plane parallel to a surface of the substrate, the method comprising:

biasing the source and the drain with a first voltage for generating a current flowing through the semiconductor channel, biasing the gate with a second voltage and controlling the current flowing through the semiconductor channel via a FET channel-gate coupling formed by the semiconductor and the at least one gate, receiving the gas in the at least one space, whereby the gas, received in the at least one space configured to receive the gas is arranged to influence at least one electrical property of the FET channel-gate coupling, sensing gas based on the influenced at least one electrical property of the FET channel-gate coupling.

15. The method according to claim 14, further comprising measuring the influenced at least one electrical property of the FET channel-gate coupling, and sensing gas based on the measured influenced at least one electrical property of the FET channel-gate coupling.

16. The method according to claim 14, further comprising providing the first layer on at least a portion of the semiconductor channel, wherein the first layer comprises nanoparticles of at least one metal selected from the group consisting of platinum, Pt, palladium, Pd, gold, Au, and nickel, Ni, measuring the current through the semiconductor channel, and determining a concentration of molecular hydrogen, $H_2$, in the gas based on the measured current.

* * * * *